US009486359B2

(12) United States Patent
Hauger et al.

(10) Patent No.: US 9,486,359 B2
(45) Date of Patent: *Nov. 8, 2016

(54) OPHTHALMIC SURGICAL SYSTEM AND CONTROL ARRANGEMENT THEREFOR (71) Applicant: Carl Zeiss Meditec AG, Jena (DE)

(72) Inventors: Christoph Hauger, Aalen (DE); Martin Kraus, Huettlingen (DE)

(73) Assignee: Carl Zeiss Meditec AG, Jena (DE)

( * ) Notice: Subject to any disclaimer, the term of this patent is extended or adjusted under 35 U.S.C. 154(b) by 378 days.

This patent is subject to a terminal disclaimer.

(21) Appl. No.: 13/851,850

(22) Filed: Mar. 27, 2013

(65) Prior Publication Data
US 2013/0218168 A1    Aug. 22, 2013

Related U.S. Application Data (63) Continuation of application No. PCT/DE2011/001777, filed on Sep. 24, 2011.

(30) Foreign Application Priority Data

Sep. 30, 2010   (DE) .................. 10 2010 047 009

(51) Int. Cl.
*A61F 9/00* (2006.01)
*A61F 9/007* (2006.01)

(52) U.S. Cl.
CPC .......... *A61F 9/00745* (2013.01); *A61B 90/361* (2016.02)

(58) Field of Classification Search
CPC ........... A61F 9/00745; A61F 9/00736; A61F 9/00754; A61F 2002/2864; A61B 19/5212
USPC ...... 604/22; 606/4, 5, 6, 107, 167, 169, 170, 606/171
See application file for complete search history.

(56) References Cited

U.S. PATENT DOCUMENTS

| | | | |
|---|---|---|---|
| 6,544,254 B1 | 4/2003 | Bath | |
| 2002/0077647 A1* | 6/2002 | Snow et al. | 606/170 |
| 2004/0152990 A1 | 8/2004 | Mackool | |
| 2008/0262505 A1* | 10/2008 | Shahoian | 606/108 |
| 2008/0319451 A1 | 12/2008 | Zacharias | |
| 2009/0306581 A1 | 12/2009 | Claus | |

OTHER PUBLICATIONS

International Search Report dated Mar. 26, 2012 of international application PCT/DE2011/001777 on which this application is based.

English translation of the Office action of the German Patent Office dated Apr. 6, 2011 in German patent application 10 2010 047 009.0 on which the claim of priority is based.

* cited by examiner

*Primary Examiner* — Jonathan Miles
(74) *Attorney, Agent, or Firm* — Walter Ottesen, P.A.

(57) ABSTRACT

A control arrangement for an ophthalmic surgical system for phacoemulsification of an eye lens includes an optical system for generating an image of an object region. At least part of the eye lens to be emulsified and part of a needle of a phacoemulsification handpiece can be arranged in the image. An image evaluation unit evaluates the generated image in such a way that an evaluation variable is generated which is dependent on a property of a particle produced by phacoemulsification of the eye lens or is dependent on a relation of the particle to its surroundings. A control unit generates a control variable in dependence upon the evaluation variable and, with the control variable, the control unit controls an absolute value of ultrasound energy which is supplied to the phacoemulsification handpiece by an energy source for phacoemulsification of the eye lens.

3 Claims, 5 Drawing Sheets

|  | GM1 < W1 | GM1 > W1 |
|---|---|---|
| GM2 < W2 | US1 | US2 |
| GM2 > W2 | US1 | US1 |

FIG.8

| | GM1 > W1 | | | |
|---|---|---|---|---|
| | OM1 | OM2 | OM3 | OM4 |
| GM2 < W2 | US2 | US3 | US4 | US5 |

FIG.9

OPHTHALMIC SURGICAL SYSTEM AND CONTROL ARRANGEMENT THEREFOR

CROSS REFERENCE TO RELATED APPLICATIONS

This application is a continuation application of international patent application PCT/DE2011/001777, filed Sep. 24, 2011, designating the United States and claiming priority from German application 10 2010 047 009.0, filed Sep. 30, 2010, and the entire content of both applications is incorporated herein by reference.

FIELD OF THE INVENTION

The invention relates to a control arrangement for an ophthalmic surgical system for phacoemulsification of an eye lens, and an ophthalmic surgical system with such a control arrangement.

BACKGROUND OF THE INVENTION

There are a number of surgical techniques for treating clouding within the eye lens, which is referred to as a cataract in medicine. The most common technique is phacoemulsification, in which a thin needle is introduced into the diseased lens and excited to vibrate by means of ultrasound. The vibrating needle emulsifies the lens in its direct vicinity in such a way that the created lens particles can be suctioned away through a line by means of a pump. In the process, a rinsing fluid (irrigation fluid) is supplied, with the particles and the fluid being suctioned away through an aspiration line, which is usually arranged within the needle. Once the lens has been completely emulsified and removed, a new artificial lens can be inserted into the empty capsular bag, and so a patient treated can thus regain good visual acuity.

Approximately 600,000 surgical procedures of this type are carried out each year in Germany alone. The rate of complication is relatively low, but this requires much experience of the performing surgeon. Furthermore, the time expenditure for emulsifying an eye lens is still relatively high. In order to be able to shorten the time needed for the surgical procedure, it is possible to let the vibrating needle operate at a higher amplitude. If this occurs without interruption, this is synonymous with a higher energy input. However, the result of this is greater heating in the vicinity of the vibrating needle. Since the needle is pierced through the cornea, a higher energy input means a stronger thermal load on the cornea. This can lead to at least partly surrounding tissue, such as, for example, the cornea, overheating and being damaged. By contrast, if the surgeon works with a needle which is only operated at a small amplitude such that there is only a small energy input into the lens and the surrounding tissue, the risk of damage to the tissue can be reduced. However, the duration of the surgical procedure then increases accordingly. If a relatively hard eye lens is present, the surgeon can only achieve emulsification by a higher energy input. However, in order to prevent burning of the tissue such as the cornea there must be frequent interruptions during the surgical procedure so that enough time is available for a cool-down.

SUMMARY OF THE INVENTION

It is an object of the invention to develop a control arrangement and an ophthalmic surgical system, by means of which a surgical procedure by phacoemulsification of an eye lens is possible in a short period of time without risking burns to the surrounding tissue. In general, the control arrangement and the ophthalmic surgical system should reduce the risk of unwanted damage to a patient's eye during a cataract surgical procedure.

According to the invention, provision is made for a control arrangement for an ophthalmic surgical system for phacoemulsification of an eye lens.

The control arrangement includes an optical system, by means of which an image can be generated of an object region, wherein at least part of the eye lens to be emulsified and part of a needle of a phacoemulsification handpiece can be arranged in the object region; an image evaluation unit, which is suitable for evaluating the generated image in such a way that at least one evaluation variable is established, which is dependent on a property of a particle, produced by phacoemulsification, of the eye lens or on a relation of the particle to its surroundings; and, a control unit, by means of which, dependent on the at least one supplied evaluation variable, it is possible to establish a control variable, wherein the control variable can control an absolute value of ultrasound energy, supplied to the phacoemulsification handpiece by means of an energy source, for phacoemulsification of the eye lens.

Ultrasound energy, which is supplied to the eye lens through a needle, therefore depends on an evaluation variable which can be established by an optical system. The evaluation variable is dependent on a property of a particle of the eye lens or a relation of the particle to its surroundings. Thus, the energy input for breaking up the eye lens is dependent on a property of a lens particle which can be captured by the optical system. Although such a control arrangement cannot completely replace the experience of a surgeon, it can achieve higher safety during the operation. In the case of a specific property of a particle or of a relation of the particle to its surroundings, an energy input can therefore be selected to be so low that the risk of cornea burn likewise is low. If the evaluation of the generated image identifies a property of a particle which requires a high energy input, this high energy input is only applied for as long as this property of the particle is present.

The optical system renders fast image processing possible, and so short reaction times are achievable for the control arrangement. As a result, it is possible to identify substantially more quickly what level of energy input is sensible than if a surgeon actuates the control of the energy input manually, for example by a foot pedal, as is the case in the prior art.

Reference is made to the fact that there is no need for a blockage (occlusion) of an aspiration line by a particle in order to be able to operate the control arrangement.

The evaluation variable from the image evaluation unit preferably is a geometric measurement variable of a particle of the eye lens to be emulsified. Here, the optical system can be arranged in such a way that a plan view of the lens to be emulsified is possible. If the area of the particle to be emulsified is selected as the geometric measurement variable of a particle, the energy for emulsification of the particle to be supplied can therefore be made to be dependent on the area of this particle. A particle which, in plan view, assumes an area which is smaller than the smallest internal diameter of the aspiration line in the needle, through which the particles are suctioned away, is already so small that the needle need only be operated with low energy or with no energy. This increases the safety against tissue overheating in the region of the needle. However, if the area of the particle is greater than the smallest internal diameter of the aspiration line, through which the particles are suctioned away, the energy source can be actuated in such a way that a relatively high absolute value of ultrasound energy is supplied for driving the needle.

Another geometric measurement variable can also be the circumference of the particle to be emulsified or the volume of the particle to be emulsified, wherein the latter measurement variable requires three-dimensional capture of the lens geometry. Another geometric measurement variable can also be a distance of an edge of a particle of the eye lens to be emulsified from a front edge of the needle or a suction opening of the aspiration line. If the particle still is relatively far away from the needle, the energy input can be selected to be low. If a distance drops below a predetermined minimum distance between the edge of the particle to be emulsified and the edge of the needle, it is however possible to increase the absolute value of the supplied energy.

According to another embodiment of the invention, the evaluation variable can also be an optical measurement variable of a particle of the eye lens to be emulsified. From experience, a medical practitioner knows that a very brightly shining particle is usually softer and hence easier to emulsify than a dark and harder particle. An optical evaluation of the image as an alternative to the geometric measurement variable, or in addition to the geometric measurement variable, can aid in setting the required energy input. The optical measurement variable is preferably a light transmissivity, a grayscale-value intensity or a color intensity.

The evaluation variable can also be a mechanical or kinematic measurement variable of a particle of the eye lens to be emulsified. The mechanical measurement variable can be the hardness of the particle. The harder a particle is the greater an energy input must be in order to emulsify the particle into small parts. This is important because it is known that an eye lens generally does not have a constant hardness within its entire volume, but rather there are zones of different hardness in the eye lens.

The optical system preferably has a light microscope and/or an optical coherence tomography (OCT) system. The OCT system can also be arranged within a light microscope such that the medical practitioner can see the area of the operation through a light microscope while the OCT system can be used to control the required energy yield.

According to one development of the invention, the optical system can also be at least partly arranged within the phacoemulsification handpiece. In this case, the optical system is preferably an OCT system, with a fiber being integrated into the phacoemulsification handpiece. The fiber can preferably have a rotating or scanning configuration in order to capture a volume region of the particle situated at the edge of the needle.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
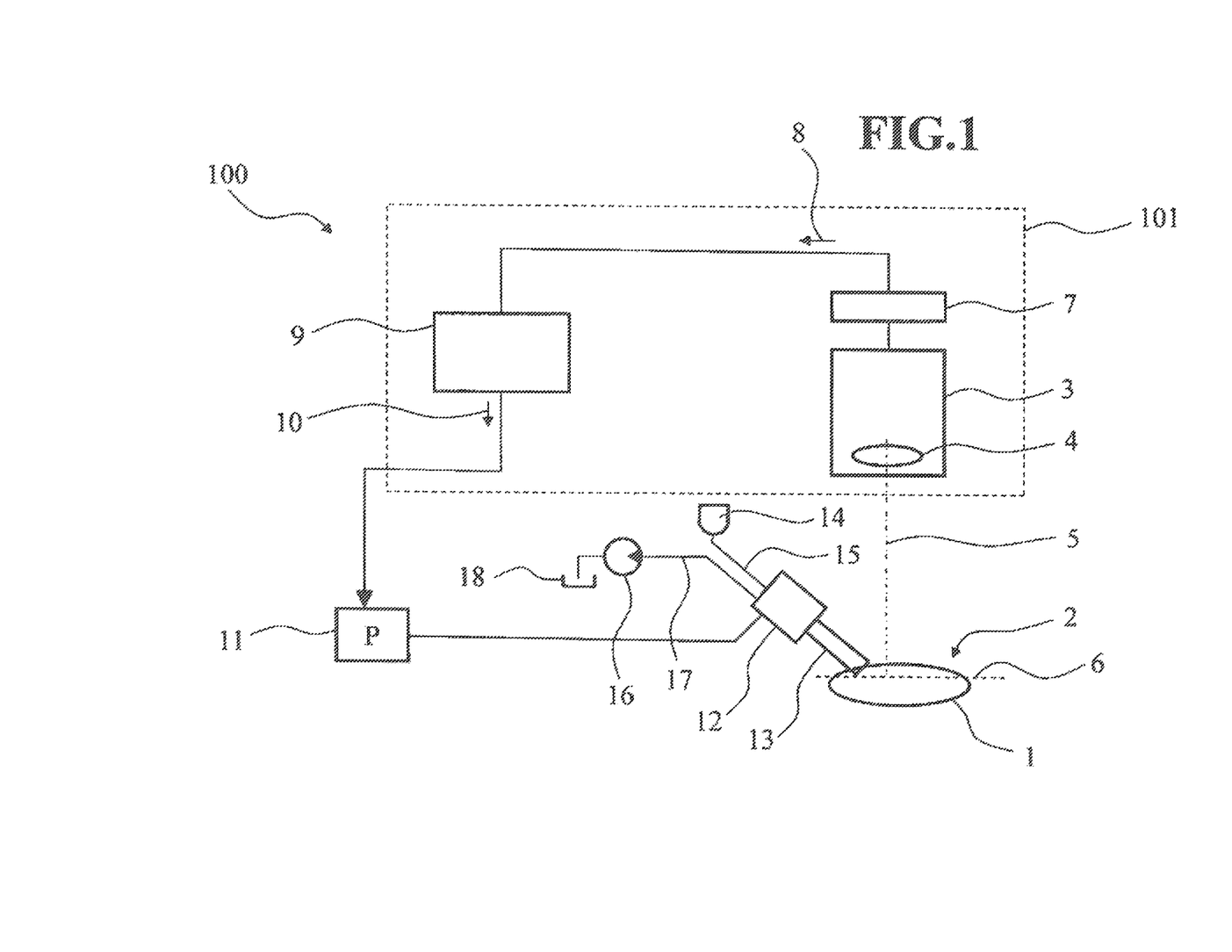
FIG. 1 shows a schematic illustration of a first embodiment of an ophthalmic surgical system with a control arrangement according to the invention.

FIG. 1 illustrates an ophthalmic surgical system 100 with a control arrangement 101 according to the invention. An eye lens 1, which is to be emulsified, is situated within an object region 2 of an optical system 3. In this embodiment, the optical system 3 is a light microscope, which has a main objective 4 with an optical axis 5. A focus plane 6 is arranged within the object region 2 of the eye lens 1. The image generated by the optical system 3 is fed to an image evaluation unit 7, which is suitable for evaluating the supplied image. The evaluation establishes at least one evaluation variable 8, which is dependent on a property of a lens particle to be produced by emulsification or on a relation of the lens particle to the surroundings thereof. The evaluation variable 8 is fed to a control unit 9, which establishes a control variable 10 dependent on the at least one supplied evaluation variable. The control variable can be fed to an energy source 11 and, from there, to a phacoemulsification handpiece 12, and so an absolute value of ultrasound energy supplied to the phacoemulsification handpiece 12 from the energy source 11 can be controlled. The control variable 10 can also be fed directly to the handpiece 12 and be processed there with the energy supplied by the energy source 11.

The ultrasound energy supplied to the phacoemulsification handpiece 12 or the associated actuators is transmitted to a needle 13, by means of which the eye lens 1 can be emulsified. During the emulsification of the eye lens 1, an irrigation fluid is routed from an irrigation container 14 through an irrigation line 15 up to the front region of the needle in the phacoemulsification handpiece. An aspiration pump 16 is used to suction away the emulsified particles and fluid to an aspiration container 18 through an aspiration line 17.

Figure 2:
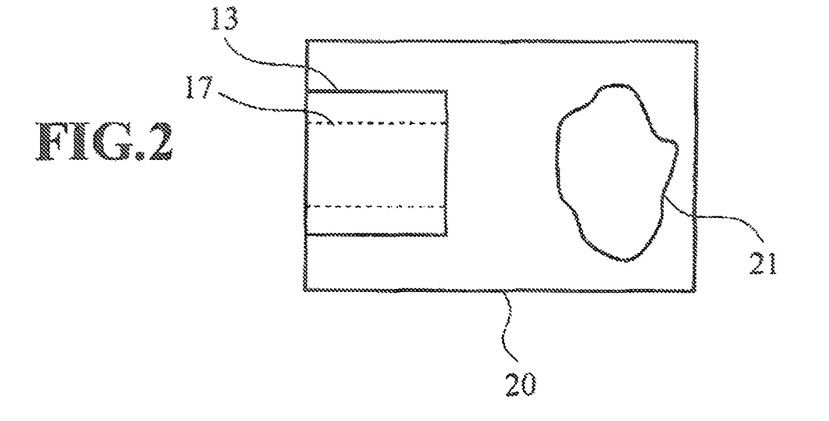
FIG. 2 shows an image from an image evaluation unit with part of a needle and a particle to be emulsified, wherein the particle is far away from the needle.
Figure 3:
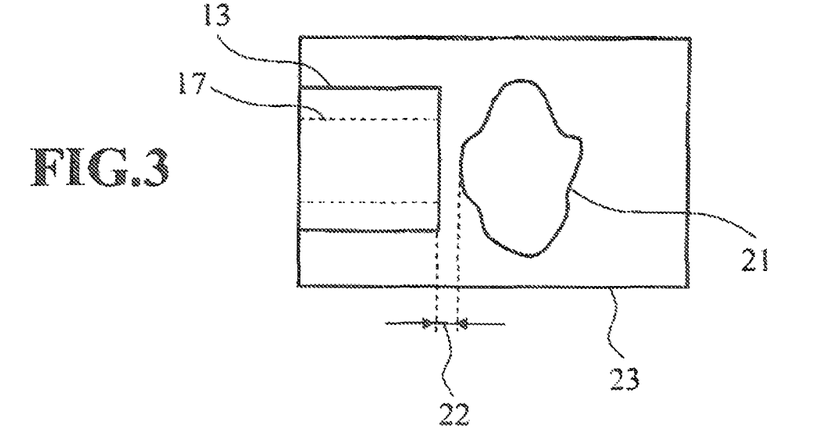
FIG. 3 shows an image from an image evaluation unit with part of a needle and a particle to be emulsified, wherein the particle is arranged very close to the needle.

FIG. 2 shows an image 20 from the image evaluation unit 7, illustrating part of a needle 13 with an aspiration line 17 contained therein and a particle 21 to be emulsified in front of the needle 13. The particle 21 still is relatively far away from the needle. FIG. 3 illustrates an image 23, in which, however, the particle 21 is arranged at a relatively close distance 22 from the needle tip 13. The image evaluation unit can now evaluate this image 23 in such a way that the distance 22 is captured and the ultrasound energy to be supplied to an energy source is controlled accordingly. By way of example, if the distance 22 is less than 100 micrometers, the needle 13 can be actuated in such a way that a greater absolute value of energy is supplied thereto. Hence, the higher absolute value of energy is only allowed if an occlusion is imminent or has already occurred.

Figure 4:
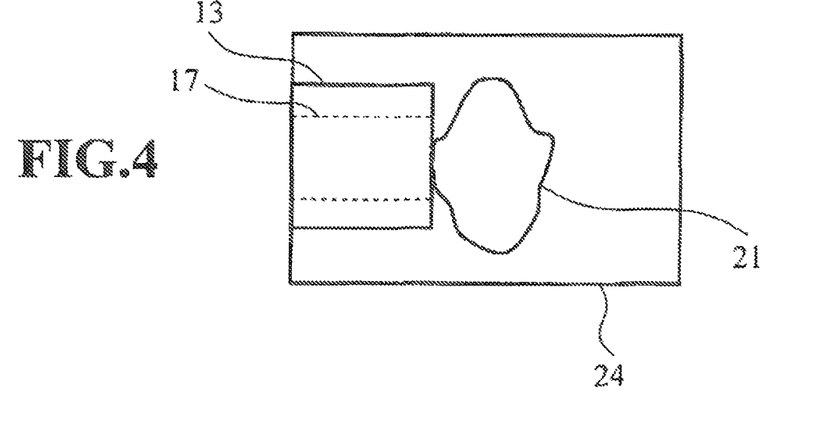
FIG. 4 shows an image from an image evaluation unit with a needle and a particle, wherein the particle touches the needle.

FIG. 4 illustrates an image 24 from an image evaluation unit 7, illustrating a front part of the needle 13 with an aspiration line 17 contained therein and a particle 21 to be emulsified, wherein the particle 21 is in direct contact with the needle 13. In this case, the distance 22 is also less than, for example, 100 micrometers, and so the needle can be operated with relatively high ultrasound energy in order to comminute the particle 21. Once this has been successfully completed and a plurality of smaller particles 31 have been formed from the particle 21 (see FIG. 5), the ultrasound energy can once again be set to a lower value.

Figure 5:
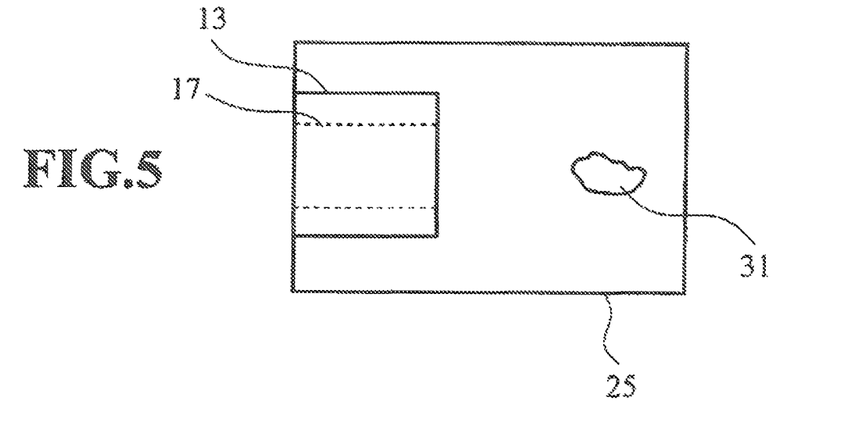
FIG. 5 shows an image from an image evaluation unit with part of a needle and a small particle, wherein the particle is far away from the needle.

FIG. 5 illustrates an image 25 with a particle 31 which is relatively far away from the needle 13. In this case, moreover, the area formed by the particle 31 is so small in plan view that it can be expected that the particle can be suctioned away without problems through the suction opening in the aspiration line 13. In the case of such an image, the control arrangement can be operated in such a way that the supplied ultrasound energy assumes a relatively low absolute value.

Figure 6:
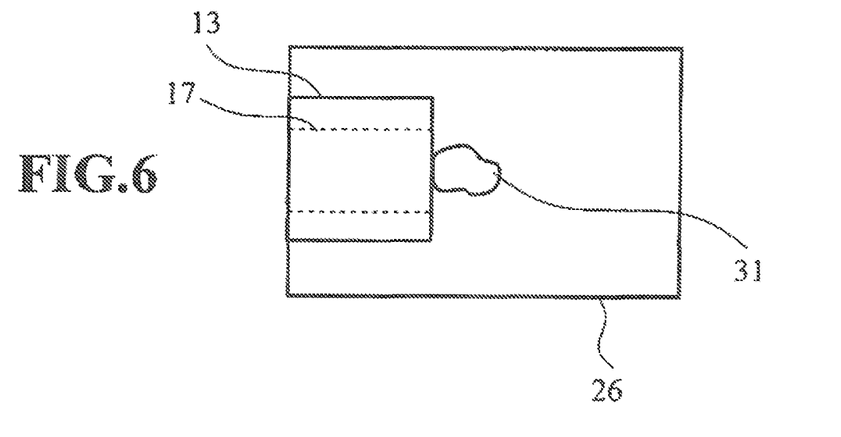
FIG. 6 shows an image from an evaluation unit with part of a needle and a small particle which is touching the needle.

In the situation illustrated in FIG. 6, an image 26 can be seen in which the particle 31 directly touches the needle 13. However, the particle 31 is so small that it can be suctioned away without problems through the aspiration line 17 of the needle 13, and so the supplied absolute value of ultrasound energy can also be kept relatively low.

Figure 7:
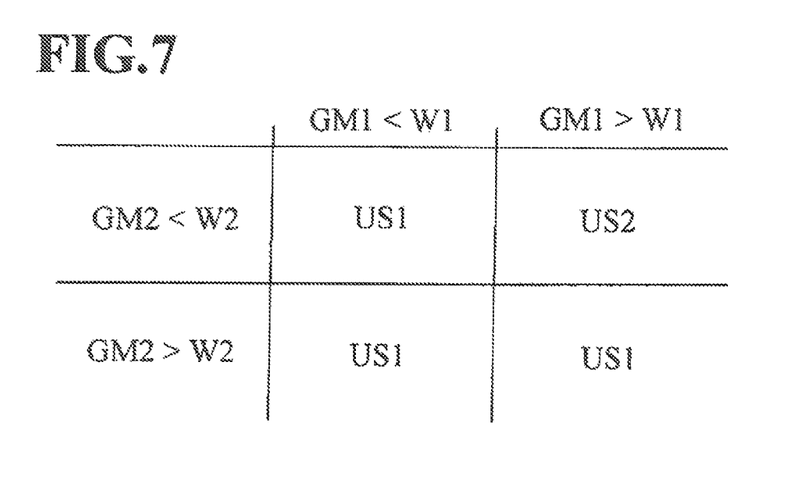
FIG. 7 shows a table for establishing an amount of ultrasound energy depending on two geometric measurement variables.

FIG. 7 illustrates a table which lists the interaction between an absolute value of ultra-sound energy to be supplied and a first geometric measurement variable GM1 and a second geometric measurement variable GM2. By way of example, the first geometric measurement variable GM1 can be an area of a particle to be emulsified within an image generated by the optical system. The second geometric measurement variable GM2 can be a distance of a particle to be emulsified from the front edge of the aspiration line 17. If GM1 is less than a predetermined variable W1, where W1 for example is the cross-sectional area in the region of the smallest internal diameter of an aspiration line 17, certain prescriptions emerge for an amount of ultrasound energy to be supplied to the needle 13, depending on the second geometric measurement variable GM2. The second geometric measurement variable GM2 can be made dependent on a second threshold W2. If GM2 is less than W2, this means that the distance between the particle to be emulsified and the needle 13 is relatively small. If GM2 is greater than W2, this means that the particle is relatively far away from the needle 13. By way of example, W2 can be the maximum amplitude of the needle 13.

Accordingly, the situations described below arise as per FIG. 7.

If GM1 is less than W1 and GM2 is less than W2, that is, if a relatively small particle is captured at a very small distance from the needle in the image from an image evaluation unit 7 (for example, FIG. 6), a first absolute value US1 of ultrasound energy can be supplied. This absolute value can have a value of zero or almost zero. By contrast, if GM1 is greater than W1, wherein GM2 remains less than W2 without change, there therefore is a relatively large particle to be emulsified relatively close to a needle 13 (see FIG. 4). In this ease, the control arrangement can be operated in such a way that a higher absolute value of ultrasound energy US2 is supplied to a needle such that the relatively large particle is broken down into small particles in the shortest time possible.

If GM1 is less than W1 and GM2 is greater than W2, that is, if a relatively small particle is arranged at a great distance from the needle 13 (see FIG. 5), it is like-wise possible to work with only a low absolute value US1 of ultrasound energy. If, as per another situation, GM1 is greater than W1 and GM2 is greater than W2, that is, if a relatively large particle still is relatively far away from the needle (see FIG. 2), it is also possible in this case to work with a low absolute value US1 of ultrasound energy. This means that, as per FIG. 7, a high energy input is only provided for the case where a large particle is relatively close to or in contact with a needle 13.

Figure 8:
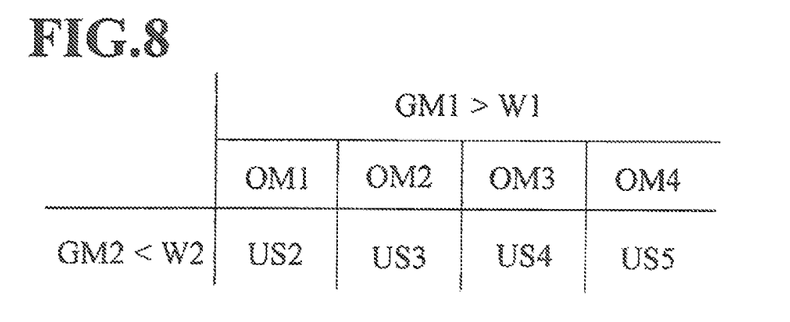
FIG. 8 shows a table for establishing an amount of ultrasound energy depending on two geometric measurement variables and an optical measurement variable.

FIG. 8 illustrates a table in which the respective absolute values of ultrasound energy are illustrated depending on a first geometric measurement variable GM1, a second geometric measurement variable GM2 and different absolute values of an optical measurement variable. By way of example, the optical measurement variable can be the light-transmittance of a particle. In the table illustrated in FIG. 8, an optical measurement variable is subdivided into four states, wherein OM1 means high transparency, OM2 means lower transparency, OM3 means even lower transparency and OM4 means an almost completely vanished transparency. If GM1 is greater than W1, that is, if a relatively large particle is present, and at the same time GM2 is less than W2, that is, if the particle is relatively close to a needle, the supplied ultrasound energy can be made to be dependent on the present transparency of the particle. If the particle has high transparency, it is possible to work with a relatively low absolute value US2 of ultrasound energy. If the particle is less transparent, that is, if the optical measurement variable has an absolute value OM2, it is possible to work with a higher absolute value US3 of ultrasound energy. If the transparency is even further reduced such that an optical measurement variable with the absolute value OM3 is present, it is possible to work with an even higher absolute value US4 of ultrasound energy. If, in the lens to be emulsified, a particle is identified which has nearly no transparency any more such that an optical measurement variable with the absolute value OM4 is established, a very high absolute value US5 of ultrasound energy can be supplied in the case where this particle is arranged relatively close to the needle, that is, when GM2 is less than W2. The reason for this grading lies in the fact that the assumption is made that as the transparency decreases, the particle to be emulsified becomes harder and more energy has to be applied to break it down into smaller particles.

Figure 9:
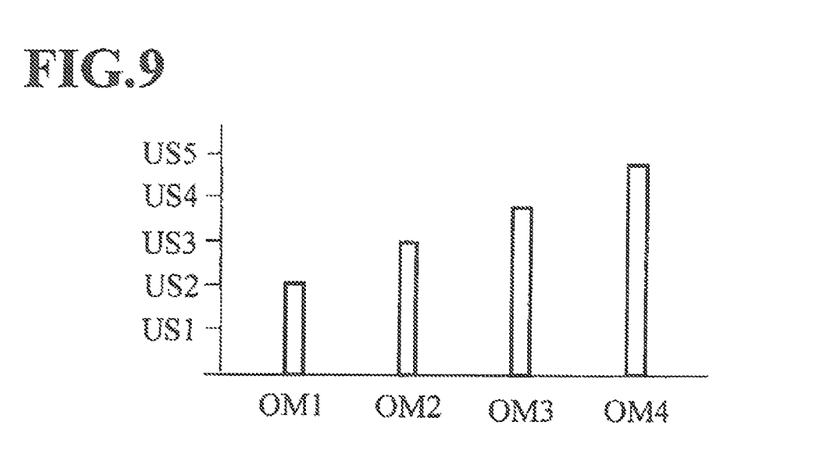
FIG. 9 shows a diagram which schematically shows a dependence between an optical measurement variable and supplied ultrasound energy; and, FIG. 10 shows a schematic illustration of a second embodiment of an ophthalmic surgical system with a control arrangement according to the invention.

FIG. 9 once again illustrates these situations illustrated in FIG. 8 more clearly in the form of a bar graph. It can be seen from FIG. 9 that an increasingly higher absolute value of ultrasound energy can be supplied as the transparency decreases.

Figure 10:
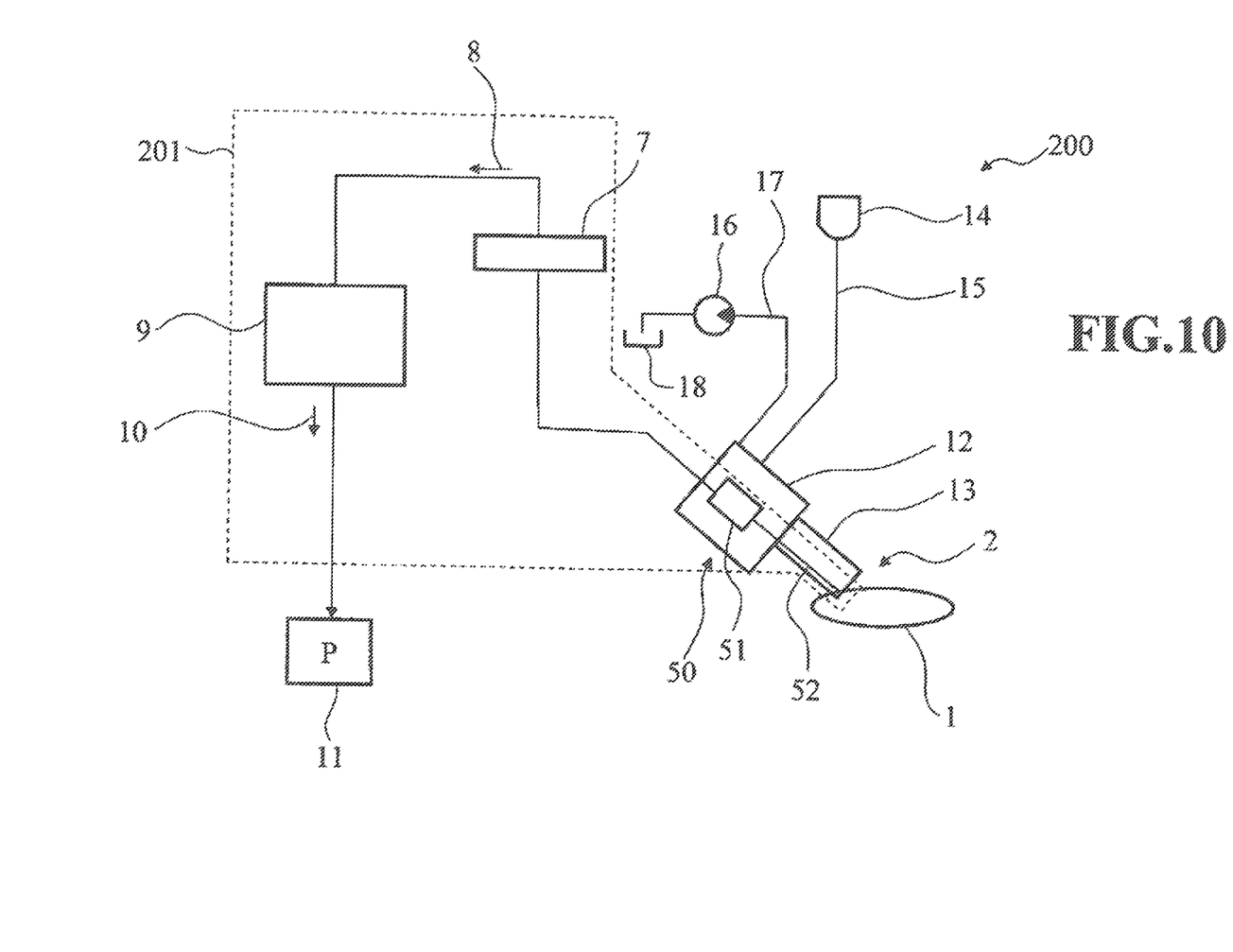

FIG. 10 illustrates a second embodiment of a control arrangement 201 for an ophthalmic surgical system 200. The ophthalmic surgical system 200 has a control arrangement 201, which has an optical system 50, an image evaluation unit 7 and a control unit 9. The optical system 50 can be present in the form of an OCT system, which has a source for temporally incoherent and spatially coherent light, additionally having a device 51 for superposing laser radiation from a sample beam path with laser radiation from a reference beam path, and furthermore has an image generation unit for generating an image. The optical system 50 furthermore has an OCT fiber 52, which is arranged in the needle 13 or on the needle 13. The image generated by the image generation unit is thereupon routed to an image evaluation unit 7 which evaluates the image, with an evaluation variable 8 being established. This evaluation variable 8 can be fed to a control unit 9 which establishes a control variable 10. The control variable 10 can subsequently act on an energy source 11 in such a way that an associated amount of ultrasound energy can be supplied to the phacoemulsification handpiece 12 or the needle 13 of the phacoemulsification handpiece 12. The ophthalmic surgical system 200 furthermore has an irrigation container 14, from which, through an irrigation line 15, fluid can be routed to the handpiece 12 and, from there, to an eye lens 1 to be treated. The emulsified particles can then, by means of a pump 16, be suctioned away through an aspiration line 17 to an aspiration container 18.

It is furthermore feasible that an ophthalmic surgical system has an optical system 3 in the form of a light microscope and an optical system 50 in the terra of an OCT system.

According to a further embodiment, an OCT system can also be arranged within a light microscope, wherein such an OCT system can additionally be arranged within a phacoemulsification handpiece.

It is understood that the foregoing description is that of the preferred embodiments of the invention and that various changes and modifications may be made thereto without departing from the spirit and scope of the invention as defined in the appended claims.

What is claimed is:

1. A control arrangement for an ophthalmic surgical system for phacoemulsification of an eye lens, the ophthalmic surgical system including a phacoemulsification handpiece having a needle; and, an ultrasound energy source for supplying ultrasound energy to said phacoemulsification handpiece; said control arrangement comprising:
   an optical system for generating an image of an object region wherein at least a part of said eye lens and a part of said needle are arranged;
   an image evaluation unit configured to evaluate said image so as to determine at least one evaluation variable dependent upon a characteristic of a particle of said eye lens generated by phacoemulsification or a relation of said particle to its surroundings;
   a control unit operatively connected to said image evaluation unit for receiving said evaluation variable;
   said control unit being configured to generate a control variable in dependence upon said evaluation variable and, with said control variable, control an absolute value of said ultrasound energy for the phacoemulsification of said eye lens;
   said evaluation variable being a geometric measurement variable of said particle of said eye lens to be emulsified; and,
   said geometric measurement variable being the area or the circumference or the volume of the particle to be emulsified in said image,
   wherein said optical system includes a light microscope and/or an optical coherence tomography (OCT) system.

2. The control arrangement of claim 1, wherein said optical system is at least partly arranged within said phacoemulsification handpiece.

3. An ophthalmic surgical system for phacoemulsificating an eye lens, the ophthalmic surgical system comprising:
   a phacoemulsification handpiece having a needle;
   an ultrasound energy source for supplying ultrasound energy to said phacoemulsification handpiece;
   an optical system for generating an image of an object region wherein at least a part of said eye lens and a part of said needle are arranged;
   an image evaluation unit configured to evaluate said image so as to determine at least one evaluation variable dependent upon a characteristic of a particle of said eye lens generated by phacoemulsification or a relation of said particle to its surroundings;
   said evaluation variable being a geometric measurement variable of said particle of said eye lens to be emulsified;
   said geometric measurement variable being the area or the circumference or the volume of the particle to be emulsified in said image;
   a control unit operatively connected to said image evaluation unit for receiving said evaluation variable; and,
   said control unit being configured to generate a control variable in dependence upon said evaluation variable and, with said control variable, control an absolute value of said ultrasound energy for the phacoemulsification of said eye lens,
   wherein said optical system includes a light microscope and/or an optical coherence tomography (OCT) system.

* * * * *

UNITED STATES PATENT AND TRADEMARK OFFICE
CERTIFICATE OF CORRECTION

| | | |
|---|---|---|
| PATENT NO. | : 9,486,359 B2 | Page 1 of 1 |
| APPLICATION NO. | : 13/851850 | |
| DATED | : November 8, 2016 | |
| INVENTOR(S) | : C. Hauger et al. | |

It is certified that error appears in the above-identified patent and that said Letters Patent is hereby corrected as shown below:

In the Specification

In Column 5:
Line 66: delete "ease" and substitute -- case -- therefor.

In Column 7:
Line 19: delete "terra" and substitute -- form -- therefor.

Signed and Sealed this
Third Day of January, 2017

Michelle K. Lee
*Director of the United States Patent and Trademark Office*